United States Patent
Thiel et al.

(10) Patent No.: US 11,384,207 B2
(45) Date of Patent: Jul. 12, 2022

(54) PREPARATION OF A CURED POLYMER COMPRISING URETHANE GROUPS AND SILICON ATOMS

(71) Applicant: BASF SE, Ludwigshafen am Rhein (DE)

(72) Inventors: Indre Thiel, Ludwigshafen (DE); Thomas Maximilian Wurm, Ludwigshafen (DE); Peter Rudolf, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/428,705

(22) PCT Filed: Feb. 7, 2020

(86) PCT No.: PCT/EP2020/053083
§ 371 (c)(1),
(2) Date: Aug. 5, 2021

(87) PCT Pub. No.: WO2020/161281
PCT Pub. Date: Aug. 13, 2020

(65) Prior Publication Data
US 2022/0041815 A1    Feb. 10, 2022

(30) Foreign Application Priority Data

Feb. 8, 2019 (EP) .................... 19156254

(51) Int. Cl.
| | | |
|---|---|---|
| *C08G 77/458* | (2006.01) | |
| *C07D 327/04* | (2006.01) | |
| *C07F 7/08* | (2006.01) | |
| *C07F 7/18* | (2006.01) | |
| *C08G 71/04* | (2006.01) | |
| *C08G 77/26* | (2006.01) | |
| *C08G 77/28* | (2006.01) | |
| *C09D 183/10* | (2006.01) | |
| *C08F 220/38* | (2006.01) | |
| *C08F 222/10* | (2006.01) | |
| *C08F 222/22* | (2006.01) | |
| *C09J 133/14* | (2006.01) | |
| *C09J 135/02* | (2006.01) | |

(52) U.S. Cl.
CPC ......... *C08G 77/458* (2013.01); *C07D 327/04* (2013.01); *C07F 7/0814* (2013.01); *C07F 7/18* (2013.01); *C07F 7/1892* (2013.01); *C08F 220/387* (2020.02); *C08F 222/1063* (2020.02); *C08F 222/22* (2013.01); *C08G 71/04* (2013.01); *C08G 77/26* (2013.01); *C08G 77/28* (2013.01); *C09D 183/10* (2013.01); *C09J 133/14* (2013.01); *C09J 135/02* (2013.01); *C08F 2800/10* (2013.01); *C08F 2800/20* (2013.01); *C08F 2810/20* (2013.01); *C08F 2810/50* (2013.01)

(58) Field of Classification Search
CPC .... C07D 327/04; C07F 7/0812; C07F 7/0814; C07F 7/18; C07F 7/1804; C08G 77/26; C08G 77/28; C08G 71/04
See application file for complete search history.

(56) References Cited

U.S. PATENT DOCUMENTS

| | | | |
|---|---|---|---|
| 3,632,557 A | 1/1972 | Brode et al. | |
| 4,625,012 A | 11/1986 | Rizk et al. | |
| 6,355,127 B1 | 3/2002 | Mahdi et al. | |
| 2019/0352461 A1 | 11/2019 | Huber et al. | |
| 2020/0354333 A1 | 11/2020 | Rudolf et al. | |
| 2021/0395439 A1* | 12/2021 | Colin ................ | C07D 327/04 |
| 2021/0395450 A1* | 12/2021 | Huber ............... | C08G 63/6956 |

FOREIGN PATENT DOCUMENTS

| | | |
|---|---|---|
| EP | 1 506 964 | 2/2005 |
| EP | 2468791 A1 | 6/2012 |
| WO | WO 98/26005 * | 6/1998 |
| WO | WO-2012/003187 A1 | 1/2012 |
| WO | 2018/042030 | 3/2018 |

(Continued)

OTHER PUBLICATIONS

U.S. Appl. No. 16/639,339, filed Feb. 14, 2020, 2020/0354333, Rudolf et al.

(Continued)

*Primary Examiner* — Marc S Zimmer
(74) *Attorney, Agent, or Firm* — Grüneberg and Myers PLLC

(57) ABSTRACT

A process prepares a cross-linked polymer containing urethane groups and silicon atoms. Starting materials of the process include a compound A) with a five-membered cyclic monothiocarbonate group, a compound B) with an amino group, selected from primary or secondary amino groups or blocked amino groups, and optionally, a compound C) with at least one functional group that reacts with a group —SH. One of the compounds contains a silicon-functional group. In one example of the process, compounds A) and B), and optionally C), are then reacted under exclusion of water to obtain a polymer with curable silicon-functional groups. The polymer is applied to a surface, gap, or a three-dimensional template. The silicon-functional groups are cured with ambient water. The polymer contains 0.001 to 0.3 mol of silicon per 100 g of the polymer.

14 Claims, No Drawings

(56) References Cited

FOREIGN PATENT DOCUMENTS

| WO | WO-2019/034468 A1 | 2/2019 |
| WO | WO-2019/034469 A1 | 2/2019 |
| WO | WO-2019/034470 A1 | 2/2019 |
| WO | WO-2019/034473 A1 | 2/2019 |

OTHER PUBLICATIONS

International Search Report dated Apr. 30, 2020 in PCT/EP2020/053083.
Written Opinion dated Apr. 30, 2020 in PCT/EP2020/053083.
Reynolds et al., "*Mercaptoethylation. II. Preparation of 2-Mercaptoethyl Carbamates and Oligoethylene Sulfides,*" Journal of Organic Chemistry, vol. 26, No. 12, Dec. 1961, pp. 5111-5115.
U.S. Office Action dated Mar. 28, 2022 in U.S. Appl. No. 16/639,204, 14 pages.
U.S. Office Action dated May 6, 2022 in U.S. Appl. No. 16/639,339, 15 pages.

\* cited by examiner

PREPARATION OF A CURED POLYMER COMPRISING URETHANE GROUPS AND SILICON ATOMS

CROSS-REFERENCE TO RELATED APPLICATIONS

This application is the National Stage entry under § 371 of International Application No. PCT/EP2020/053083, filed on Feb. 7, 2020, and which claims the benefit of priority to European Application No. 19156254.5, filed on Feb. 8, 2019. The content of each of these applications is hereby incorporated by reference in its entirety.

BACKGROUND OF THE INVENTION

Field of the Invention

Object of the present invention is a process for the preparation of a cross-linked polymer comprising urethane groups and silicon atoms, wherein a) a compound A) with at least one five-membered cyclic monothiocarbonate group and a compound B) with at least one amino group, selected from primary or secondary amino groups or blocked primary or secondary amino groups, hereinafter referred to as amino groups, and optionally a compound C) with at least one functional group that reacts with a group —SH are used as starting materials, whereby at least one of the compounds used as starting material comprises a silicon-functional group, and wherein compounds A), B) and optionally C) are processed as follows by b1) reacting compounds A) and B) and optionally C) under exclusion of water to obtain a polymer with silicon-functional groups that are still curable and b2) applying the polymer obtained in b1) to a surface, gap or a three-dimensional template and curing the silicon-functional groups with ambient water or, alternatively, c1) applying the compounds A) and B) and optionally C) to a surface, gap or a three-dimensional template and c2) reacting the compounds and curing the silicon-functional groups with ambient water in one step, or, alternatively, d1) applying a compound A) with a silicon-functional group or a compound B) with a silicon-functional group or a compound C) with a silicon-functional group or a mixture of such a compound with further compounds A) to C), whereby such mixture does not comprise compounds A) and B) in combination, to a surface, gap or a three-dimensional template and d2) curing the silicon-functional groups with ambient water and d3) then adding the missing compounds A), B) and optionally C) and reacting these compounds.

Description of Related Art

Polyurethanes are important industrial polymers. They have very good mechanical properties and are therefore used in many technical applications, for example, as foam or as binder in coatings or adhesives.

Polyurethanes have been modified with silyl groups, which are notably alkoxysilane groups. Such silyl-modified polyurethanes are moisture curable and have been used, for example, as one-component binder or resin in coatings or adhesives.

According to U.S. Pat. No. 3,632,557 silicon-terminated polyurethanes are obtained by reacting an isocyanate terminated prepolymer with an aminosilane.

U.S. Pat. Nos. 4,625,012 and 6,355,127 B1 disclose the use of isocyanato-organosilanes to obtain silyl-modified polyurethanes.

In WO 2012/003187 A1 silicon compounds with a hydrogen-silicon bond and a cross-linkable group are used to modify polyurethanes.

There is a demand to find alternative polymers with urethane groups and moisture curable silyl groups. Alternative polymers may comprise, for example, additional heteroatoms or functionalities which improve the technical application of such polymers or allow to extend the field of technical applications.

There is also a demand to find new processes for the preparation of silyl-modified polyurethanes, notable processes that does not involve the use of isocyanates.

The object of EP 2468791 A1 are epoxy compositions that comprise compounds with five-membered cyclic ring systems comprising oxygen and sulfur.

D. D. Reynolds, D. L. Fields and D. L. Johnson, Journal of Organic Chemistry, 1961, page 5111 to 5115, disclose compounds with a five-membered cyclic monothiocarbonate ring system and reactions thereof. Inter alia a reaction with an amino compound is mentioned.

WO 2019/034468 A1 and WO 2019/034469 A1 relate to a process for the synthesis of compounds with at least one monothiocarbonate group.

WO 2019/034470 A1 and WO 2019/034473 A1 relate to polymers which are obtained by reacting compounds with at least one monothiocarbonate group.

SUMMARY OF THE INVENTION

It was an object of this invention to provide alternative silyl-modified polymers and an alternative process for the preparation of silyl-modified polyurethanes. The alternative process should be economic and flexible, thus allowing the easy preparation of silyl-modified polyurethanes suitable for a variety of technical applications.

Accordingly, a process and silyl modified polymers comprising urethane and thioether groups have been found.

The invention relates to a process for the preparation of a cross-linked polymer comprising urethane groups and silicon atoms, wherein a) a compound A) with at least one five-membered cyclic monothiocarbonate group and a compound B) with at least one amino group, selected from primary or secondary amino groups or blocked primary or secondary amino groups, hereinafter referred to as amino groups, and optionally a compound C) with at least one functional group that reacts with a group —SH are used as starting materials, whereby at least one of the compounds used as starting material comprises a silicon-functional group, and wherein compounds A), B) and optionally C) are processed as follows by b1) reacting compounds A) and B) and optionally C) under exclusion of water to obtain a polymer with silicon-functional groups that are still curable and b2) applying the polymer obtained in b1) to a surface, gap or a three-dimensional template and curing the silicon-functional groups with ambient water, or, alternatively, c1) applying the compounds A) and B) and optionally C) to a surface, gap or a three-dimensional template and c2) reacting the compounds and curing the silicon-functional groups with ambient water in one step, or, alternatively, d1) applying a compound A) with a silicon-functional group or a compound B) with a silicon-functional group or a compound C) with a silicon-functional group or a mixture of such a compound with further compounds A) to C), whereby such mixture does not comprise compounds A) and B) in combination, to a surface, gap or a three-dimensional template and d2) curing the silicon-functional groups with ambient water and d3) then adding the missing compounds A), B) and optionally C) and reacting these compounds.

In a further aspect, the invention relates to coatings, sealed materials or molded bodies obtainable by the process, as defined herein.

In a further aspect, the invention relates to a polymer derived of compounds A), B) and optionally C) comprising 0.001 to 0.3 mol of silicon per 100 g of the polymer.

In a further aspect, the invention relates to a compound comprising one or two five-membered cyclic monothiocarbonate groups and one alkoxysilane group —$SiR^{1s}R^{2s}R^{3s}$.

DETAILED DESCRIPTION OF THE INVENTION

To compound A)

Compound A) comprises at least one five-membered cyclic monothiocarbonate group.

The five-membered cyclic monothiocarbonate group is a ring system with 5 members, three of them are from the monothiocarbonate —O—C(=O)—S— and the further two members are carbon atoms closing the five-membered cycle.

Compound A) may be a low molecular compound or a polymeric compound and may comprise, for example, up to 1000, notably up to 500, preferably up to 100 five-membered cyclic monothiocarbonate groups.

In a preferred embodiment, compound A) comprises one to three cyclic monothiocarbonate groups.

In a most preferred embodiment, compound A) comprises one or two five-membered cyclic monothiocarbonate groups.

Preferred compounds A) have a molecular weight of up to 10000 g/mol, notably up to 5000 g/mol and particularly up to 1000 g/mol. Most preferred are compounds A) having a molecular weight of up to 500 g/mol.

Compounds A) may comprise other functional groups, for example, non-aromatic, ethylenically unsaturated groups, ether groups, thioether groups or carboxylic ester groups or a silicon-functional group.

In a preferred embodiment, compounds A) do not comprise other functional groups than cyclic monothiocarbonate groups, non-aromatic, ethylenically unsaturated groups, ether groups, thioether groups or carboxylic ester groups or silicon-functional groups.

Preferred compounds A) are compounds of formula (I)

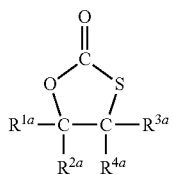

with $R^{1a}$ to $R^{4a}$ independently from each other representing hydrogen or an organic group with up to 50 carbon atoms, whereby, alternatively, $R^{2a}$, $R^{4a}$ and the two carbon atoms of the thiocarbonate group may also together form a five to ten membered carbon ring;

or compounds of formula (II)

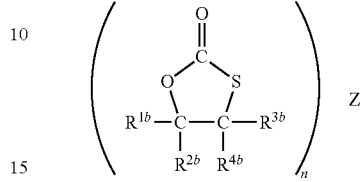

with $R^{1b}$ to $R^{4b}$ independently from each other representing hydrogen or an organic group with up to 50 carbon atoms, whereby, alternatively, $R^{2b}$, $R^{4b}$ and the two carbon atoms of the monothiocarbonate group may also together form a five to ten membered carbon ring, and with one of the groups $R^{1b}$ to $R^{4b}$ being a linking group to Z, n representing an integral number of at least 2, and Z representing a n-valent organic group.

To compounds A) of formula (I)

Compounds A) of formula (I) have one five-membered cyclic monothiocarbonate group, only.

In case that any of $R^{1a}$ to $R^{4a}$ represent an organic group, such organic group is preferably an organic group with up to 30, more preferably up to 20 carbon atoms. In a further preferred embodiment $R^{2a}$ and $R^{4a}$ do not form a five to ten membered carbon ring together with the two carbon atoms of the thiocarbonate group.

In case that any of $R^{1a}$ to $R^{4a}$ represent an organic group, such organic group may comprise heteroatoms and functional groups as listed above. In particular, it may comprise oxygen, nitrogen, sulfur, silicon and chloride. $R^{1a}$ to $R^{4a}$ may comprise oxygen, for example, in form of ether groups, hydroxy groups, aldehyde groups, keto groups or carboxy groups. In a preferred embodiment, the organic group is an aliphatic organic group with up to 30 carbon atoms which may comprise oxygen, nitrogen or chloride, in particular oxygen.

The term "halogenide", as used herein, is the trivial name of a covalently bonded halogen atom, preferably a Cl atom.

The term "chloride", as used herein, is the trivial name of a covalently bonded Cl atom.

In a more preferred embodiment, the organic group is selected from an alkyl group, from a group —$CH_2$—O—$R^{5a}$ or a group —$CH_2$—O—C(=O)—$R^{6a}$ or a group —$CH_2$—$NR^{7a}R^{8a}$ with $R^{5a}$ to $R^{8a}$ being an organic group with up to 30 carbon atoms, preferably up to 20 carbon atoms. In particular, $R^{5a}$ to $R^{8a}$ represent an aliphatic or aromatic group, which may comprise oxygen, for example, in form of ether groups. In a preferred embodiment, $R^{5a}$ to $R^{8a}$ represent an aliphatic hydrocarbon group, such as an alkyl group with 1 to 10 carbon atoms, an alkoxy group or a poly-alkoxy group. In a most preferred embodiment, $R^{5a}$ to $R^{8a}$ represent an aliphatic hydrocarbon group, notably an alkyl group with 1 to 10 carbon atoms.

In a most preferred embodiment, the organic group is a group —$CH_2$—O—$R^{5a}$ or a group —$CH_2$—O—C(=O)—$R^{6a}$.

Preferably, two to all four of $R^{1a}$ to $R^{4a}$ in formula (I) represent hydrogen, and the remaining groups $R^{1a}$ to $R^{4a}$ represent an organic group.

More preferably, two or three of $R^{1a}$ to $R^{4a}$ in formula (I) represent hydrogen, and the remaining groups $R^{1a}$ to $R^{4a}$ represent an organic group.

Most preferably, three of $R^{1a}$ to $R^{4a}$ in formula (I) represent hydrogen, and the remaining group of $R^{1a}$ to $R^{4a}$ represents an organic group. In a preferred embodiment, $R^{1a}$ or $R^{2a}$ is the remaining group representing an organic group.

As preferred compounds A) with one five-membered cyclic monothiocarbonate group may be mentioned, for example, compounds A) of formulae

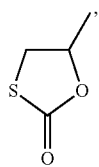
(Ia)

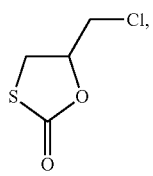
(Ib)

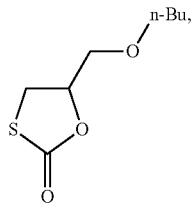
(Ic)

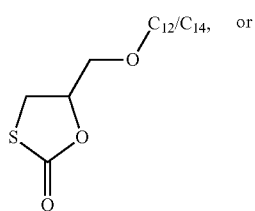
(Id)

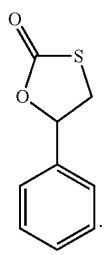
(Ie)

The substituent "$C_{12}/C_{14}$" means a substituent derived from $C_{12}/C_{14}$ fatty alcohol.

To compounds A) of formula (II)

Compounds A) of formula (II) have at least two five-membered cyclic monothiocarbonate groups.

In case that any of $R^{1b}$ to $R^{4b}$ represent an organic group, such organic group is preferably an organic group with up to 30 carbon atoms. In a further preferred embodiment, $R^{2b}$ and $R^{4b}$ do not form a five to ten membered carbon ring together with the two carbon atoms of the thiocarbonate group.

In case that any of $R^{1b}$ to $R^{4b}$ represent an organic group, such organic group may comprise other elements than carbon and hydrogen. In particular, it may comprise oxygen, nitrogen, sulfur, silicon and chloride. In a preferred embodiment, the organic group may comprise oxygen or chloride. $R^{1b}$ to $R^{4b}$ may comprise oxygen, for example, in form of ether groups, hydroxy groups, aldehyde groups, keto groups or carboxy groups.

One of the groups $R^{1b}$ to $R^{4b}$ is the linking group to Z.

Preferably, the linking group is simply a bond or a group $CH_2$—, $CH_2$—O— or $CH_2$—O—C(=O)— or $CH_2$—$NR^{5b}$— with $R^{5b}$ being an aliphatic group, notably an alkyl group with at maximum 20 carbon atoms.

More preferably, the linking group is simply a bond or a group $CH_2$— or a group $CH_2$—O— or a group $CH_2$—O—C(=O)—.

In a most preferred embodiment, the linking group is a group $CH_2$—O—.

Preferably, two or three of the groups $R^{1b}$ to $R^{4b}$ in formula (II) are hydrogen.

In a most preferred embodiment, three of the groups $R^{1b}$ to $R^{4b}$ represent hydrogen, and the remaining group of $R^{1b}$ to $R^{4b}$ is the linking group to Z.

In a most preferred embodiment, groups $R^{1b}$ or $R^{2b}$ is the linking group to Z.

n represents an integral number of at least 2. For example, n may be an integral number from 2 to 1000, specifically from 2 to 100, respectively 2 to 10.

In a preferred embodiment, n is an integral number from 2 to 5, in particular n is 2 or 3.

In a most preferred embodiment, n is 2.

Z represents a n-valent organic group. In case of a high number of n, such as, for example, 10 to 1000, Z may be a polymeric group, in particular a polymer-backbone, obtained, for example, by polymerization or copolymerization, such as radical polymerization of ethylenically unsaturated monomers, polycondensation or polyaddition. For example, polyesters or polyamides are obtained via polycondensation under elimination of water or alcohol, and polyurethanes or polyureas are obtained via polyaddition.

Such compounds of formula (II) are, for example, polymers obtained by radical polymerization or copolymerization of ethylenically unsaturated monomers comprising monothiocarbonate groups or of monomers comprising epoxy groups which are then transferred into a monothiocarbonate group.

In a preferred embodiment, Z is a n-valent organic group with up to 50 carbon atoms, in particular up to 30 carbon atoms, and which may comprise other elements than carbon and hydrogen, and n is an integral number from 2 to 5, notably 2 or 3, most preferred 2.

In a particularly preferred embodiment, Z is a n-valent organic group with up to 50 carbon atoms, in particular up to 30 carbon atoms, and which comprises carbon, hydrogen and optionally oxygen, only and no further elements, and n is an integral number from 2 to 5, notably 2 or 3, most preferred 2.

In a preferred embodiment, Z is a polyalkoxylene group of formula (G1)

$$(V-O-)_m V$$

wherein V represents a $C_2$-$C_{20}$-alkylene group, and m is an integral number of at least 1. The terminal alkylene groups V are bonded to the linking group, which is one of the groups $R^{1b}$ to $R^{4b}$, see above.

Preferably, the $C_2$-$C_{20}$-alkylene group is a $C_2$-$C_4$-alkylene group, in particular ethylene or propylene. m may, for example, be an integral number from 1 to 100, in particular from 1 to 50.

In a further preferred embodiment, Z is a group of formula (G2)

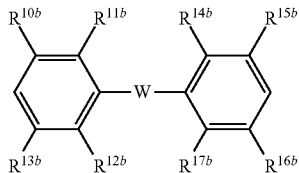

wherein W is a bi-valent organic group with at maximum 10 carbon atoms, and n is 2, and $R^{10b}$ to $R^{17b}$ independently from each other represent H or a $C_1$-$C_4$-alkyl group, and wherein the two hydrogen atoms in the para position to W are replaced by the bond to the linking group, which is one of the groups $R^{1b}$ to $R^{4b}$, see above.

Preferably, at least six of $R^{10b}$ to $R^{17b}$ are hydrogen. In a most preferred embodiment, all of $R^{10b}$ to $R^{17b}$ are hydrogen.

Groups W are, for example:

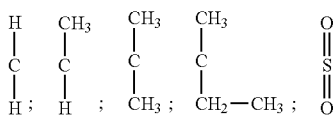

Preferably, W is an organic group that consists of carbon and hydrogen, only.

Most preferred W is

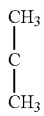

which corresponds to the structure of bisphenol A.

In a further preferred embodiment, Z is a group G3, wherein G3 represents an alkylene group, notably a $C_2$-$C_8$-alkylene group; preferred examples of such an alkylene group are ethylene ($CH_2$—$CH_2$), n-propylene ($CH_2$—$CH_2$—$CH_2$) and notably n-butylene ($CH_2$—$CH_2$—$CH_2$—$CH_2$).

Compounds A) with at least two five-membered cyclic monothiocarbonate groups are, for example, compounds of formula (III)

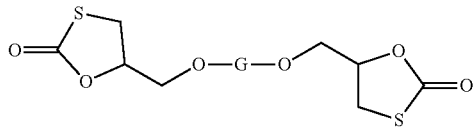

wherein G represents an alkylene group with 2 to 10, notably 2 to 6 carbon atoms.

A preferred compound of formula (III) is bis-1,3-oxathio-lane-2-one-5,5'-[1,4-butanediylbis(oxymethylene)] which has the formula

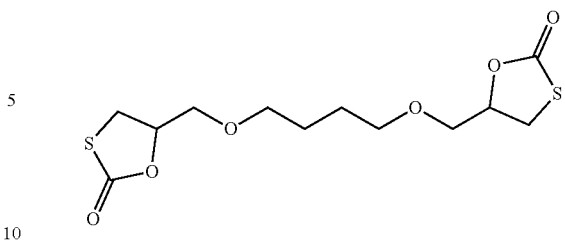

Compound A) may be a mixture of different compounds A). Compound A), respectively the mixture of compounds A), is liquid at 21° C., 1 bar. In one preferred embodiment, the liquid compound A) is obtained by solving a compound A) which is solid at 21° C., 1 bar in a compound A) which is liquid at 21° C., 1 bar.

In a preferred embodiment, compound A) is liquid at 21° C., 1 bar.

To the synthesis of compounds A)

Some methods for the synthesis of compounds with one monothiocarbonate group are described in the state of the art.

According to U.S. Pat. Nos. 3,072,676 and 3,201,416 ethylene monothiocarbonates may be prepared by a two-step-process. In a first step mercaptoethanol and chloro-carboxylates are reacted to give hydroxyethylthiocarbonate, which is heated in the second step in the presence of a metal salt catalyst to the ethylene monothiocarbonate.

According U.S. Pat. No. 3,517,029 alkylene monothio-carbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonyl sulfide. The availability of carbonyl sulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low, and by-products from polymerization are observed.

A preferred process for the preparation of compounds A) and C) is a process, wherein a) a compound with at least one epoxy group (shortly referred to as epoxy compound) is used as starting material;

b) the compound is reacted with phosgene or an alkyl chloroformate thus giving an adduct; and c) the adduct is reacted with a compound comprising anionic sulfur to give the compound with at least one five-membered cyclic monothiocarbonate groups.

This process is in detail described in WO 2019/034469 A1.

To compound B)

Compound B) is a compound with at least one amino group, selected from a primary or a secondary amino group. In this patent application the word "amino group" shall mean a primary or secondary amino group, if not indicated otherwise or obvious from the content otherwise.

Compounds B) do not comprise any monothiocarbonate groups.

Compound B) may have, for example, a molecular weight of up to 500,000 g/mol. The latter might be the case if compound B) is a high molecular compound such as a polymer comprising amino groups. In case of a polymer the term "molecular weight" means the number average molecular weight Mn, as determined by GPC against polystyrene as standard.

Compound B) may be, for example, a urethane groups comprising adduct obtained by reacting compounds with cyclic monothiocarbonate groups and compounds with primary or secondary amino groups, whereby the amino groups are in stoichiometric excess compared to the monothiocarbonate groups, thus giving a urethane groups comprising adduct which still has primary or secondary amino groups but no monothiocarbonate groups.

Preferred compounds B) have a molecular weight of up to 10000 g/mol, notably of up to 5000 g/mol and particularly of up to 1000 g/mol. Most preferred are compounds B) having a molecular weight of from 60 g/mol to 500 g/mol.

Compounds B) may comprise, for example, polymerizable, ethylenically unsaturated groups, ether groups, carboxylic ester groups or silicon-functional groups.

In a preferred embodiment, compounds B) do not comprise any other functional groups than primary or secondary amino groups, tertiary amino groups, polymerizable, ethylenically unsaturated groups, ether groups or silicon-functional groups.

In a preferred embodiment, compounds B) comprise 1 to 10 amino groups, preferably 1 to 5, respectively 1 to 3 amino groups, and, in a most preferred embodiment, compound B) comprises 1 to 2 amino groups.

In a preferred embodiment, at least one of the amino groups of compound B) is a primary amino group.

In a most preferred embodiment, all amino groups of compound B) are primary amino groups.

Compounds B) with one amino group are, for example, monoalkylamines with a primary amino group such as $C_1$-$C_{20}$-alkylamines or cycloalkyl-amines or etheramines such as 2-methoxyethylamine or 3-methoxypropylamine or di- or polyether amines such as di- or polyglycol amine or polyoxypropylene amine.

Compounds B) with more than one amino group are, for example, alkylene diamines or alkylene polyamines such as ethylene diamine, propylene diamine, butylene diamine, pentamethylene diamine, hexamethylene diamine, neopentane diamine, octamethylene diamine, 1,3-diaminopentane, or 2-methylpentan-1,5-diamine;

alkylene diamines or alkylene polyamines comprising ether groups (polyetheramine) such as polyglycol diamine or polyoxypropylene diamine;

cycloaliphatic diamines, such as cyclohexyldiamines, for example, 1,2-diaminocyclohexane, 1-methyl-2,4-diaminocyclohexane, 1-methyl-2,6-diaminocyclohexane or mixtures thereof, isophorone diamine, bis(4-aminocyclohexyl)-methane, 1,3-bis(aminomethyl)-cyclohexane, 1,4-bis(aminomethyl)-cyclohexane, 2,5-bisaminomethyl tetrahydrofuran, or 3,3'-dimethyl-4,4'-diamino-dicyclohexylmethane;

aromatic diamines, such as 1,2-phenylene-diamine or 1,4-phenylene-diamine, toluene diamines, 4,4'-diamino-diphenylmethane, 4,4'-diaminodiphenylsulfone, or 2,5-bisaminomethyl furan.

Compounds B) may also be used in a form, wherein the amino groups are protected with a protecting group. As soon as it becomes necessary or desired the protecting group is removed so that the compounds B) above with free amino groups are obtained. Usually, removal of the protecting groups occurs under the conditions of the reaction. Usual protected amino groups for amino groups are, for example, ketimines, aldimines, imidazolidines, oxazolidines, lewis acid complexed amines, carbamates, benzyloxycarbonyl amines, acyloximes, or formanilides. The deprotecting reaction can, for example, be triggered by either temperature, light, pH or the presence of water/humidity.

Further suitable compounds B) are, for example, listed in WO 2019/034470 A1 and WO 2019/034473 A1.

Compound B) may be a mixture of different compounds B).

To compound C)

Compounds C) are compounds with at least one functional group that reacts with a thiol group —SH.

Compounds C) do not comprise five-membered cyclic monothiocarbonate groups and do not comprise amino groups.

Compounds C) may have, for example, a molecular weight of up to 500,000 g/mol. The latter might be the case if compound C) is a high molecular compound such as a polymer.

Preferred compounds C) have a molecular weight of up to 10000 g/mol, notably of up to 5000 g/mol and particularly of up to 1000 g/mol. Most preferred are compounds C) having a molecular weight of from 60 g/mol to 500 g/mol.

Compounds C) may have, for example, up to 1000 functional groups that react with a group —SH, notably up to 500 and preferably up to 100 functional groups that react with a group —SH.

In a preferred embodiment, compound C) comprises 1 to 10, notably 2 to 6 functional groups that react with a group —SH.

In a most preferred embodiment, compound C) comprises 2 or 3 functional groups that react with a group —SH.

In a preferred embodiment, the reaction of the functional group of compound C) with the group —SH results in the formation of a sulfur-carbon bond.

The reaction of the functional group of compound C) with the group —SH may be an addition reaction, a condensation reaction or a nucleophilic substitution reaction.

Compounds C), that undergo an addition reaction with the group —SH are, for example, compounds with non-aromatic, ethylenically unsaturated groups or compounds with epoxy groups or compounds with isocyanate groups as functional groups. Non-aromatic, ethylenically unsaturated groups are non-aromatic carbon-carbon double bonds or carbon-carbon triple bonds.

Compounds C), that undergo a condensation reaction with the group —SH are, for example, compounds with carbonyl groups as functional group, for example, monocarbonyl compounds or dicarbonyl compounds such as dialdehydes or diketones.

Compounds C), that undergo a nucleophilic substitution reaction with the group —SH are, for example, compounds with a halogenide, notably chloride, as functional group.

Preferred functional groups that react with a group —SH are non-aromatic, ethylenically unsaturated groups or epoxy groups.

Preferred examples of a polymerizable, ethylenically unsaturated group are the vinyl group $H_2C=CH-$, the olefinic group —HC=CH—, wherein the two carbon atoms of the double bond are each substituted by one hydrogen, only, and the further substituents are notably carbon atoms, including carbon atoms of a cyclic system, and the acrylic or methacrylic group, shortly referred to as (meth)acrylic group. In this patent application the term "vinyl group" does not include the (meth)acrylic group.

Particularly preferred compounds C) are compounds with vinyl groups, (meth)acrylic groups or epoxy groups.

Compounds with vinyl groups, (meth)acrylic groups or epoxy groups are well known.

Suitable compounds C) are listed, for example, in WO 2019/034470 A1 and WO 2019/034473 A1.

Compound C) may be a mixture of different compounds C).

To the silicon-functional group

At least one of the compounds reacted comprises a silicon-functional group.

In case that compounds A) and B) are reacted, at least one of compounds A) or B) comprises a silicon-functional group.

In case that compounds A), B) and C) are reacted, at least one of compounds A), B) or C) comprises a silicon-functional group.

More than one compound of A) and B), respectively A), B) and C) may comprise a silicon-functional group. Usually only one of the compounds reacted will be a compound comprising a silicon-functional group.

As mentioned already above, compounds A), B) and C) may be mixtures of different compounds A), B) and C). Hence, the desired content of silicon-functional groups in the polymer obtained from compounds A), B) and optionally C) can easily be obtained by using mixtures of compounds with silicon-functional groups and without silicon-functional groups.

In a preferred embodiment, compounds B) comprise a silicon-functional group.

The silicon-functional group is preferably a group with at least one silicon atom and at least one group that is cross-linkable through a silanol cross-linking reaction.

The silicon-functional group may comprise more than one silicon atoms. The silicon atoms may be bonded to each other directly or via an oxygen bridge. In a preferred embodiment, the silicon-functional group comprises 1 to 3 silicon atoms. Most preferred are silicon-functional groups with only one silicon atom.

Groups that are cross-linkable through a silanol cross-linking reaction are preferably the hydroxy group and hydrolysable groups, notably alkoxy groups; alkoxy groups are preferred, notably $C_1$-$C_{10}$-alkoxy groups.

The silicon-functional group may comprise more than one group which is cross-linkable through a silanol cross-linking reaction. The possible number of groups which are cross-linkable through a silanol cross-linking reaction depends on the number of silicon atoms in the silicon-functional group.

The silicon-functional groups may, in addition, comprise hydrogen or alkyl groups that are bonded to the silicon atoms. In a preferred embodiment, the silicon-functional groups may comprise alkyl groups but does not comprise hydrogen that is bonded to the silicon atoms.

Preferably, the silicon-functional groups do not comprise any other constituents than silicon, groups which are cross-linkable through a silanol cross-linking reaction, hydrogen or alkyl groups that are all bonded to silicon and oxygen as possible bridge between silicon atoms.

Most preferably, the silicon-functional group is an alkoxysilane group of formula

wherein at least one of the groups $R^{1s}$ to $R^{3s}$ is an alkoxy group, and the other groups $R^{1s}$ to $R^{3s}$ are hydrogen or an alkyl group.

The alkoxy group is preferably a $C_1$-$C_{10}$-alkoxy group, notably a $C_1$-$C_4$-alkoxy group, for example, a butoxy group, a propoxy group, a ethoxy group or a methoxy group. Most preferably, the alkoxy group is an ethoxy group or methoxy group.

The alkyl group is preferably a $C_1$-$C_{10}$-alkyl group, notably a $C_1$-$C_4$-alkyl group, for example, a butyl group, a n-propyl group, an ethyl group or a methyl group. Most preferably, the alkyl group is an ethyl group or a methyl group.

Preferably, two or three of the groups $R^{1s}$ to $R^{3s}$ are an alkoxy group, and the remaining groups $R^{1s}$ to $R^{3s}$ are hydrogen or an alkyl group.

More preferably, two or three of the groups $R^{1s}$ to $R^{3s}$ are an alkoxy group, and any remaining group $R^{1s}$ to $R^{3s}$ is an alkyl group.

Most preferably, all three groups $R^{1s}$ to $R^{3s}$ are alkoxy groups.

Preferred compounds A) with a silicon-functional group comprise one or two five-membered cyclic monothiocarbonate groups, particularly one five-membered cyclic monothiocarbonate group, and one alkoxysilane group $-SiR^{1s}R^{2s}R^{3s}$.

Particularly preferred compounds are compounds of formula (IV)

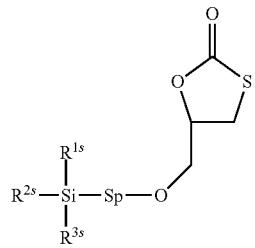

wherein $R^{1s}$ to $R^{3s}$ have the meaning above, and Sp is a spacer group, which is an organic group with 1 to 20, notably 1 to 10, preferably 1 to 6, notably 1 to 3 carbon atoms.

Sp may comprise other atoms than carbon and hydrogen, for example, nitrogen, oxygen or sulfur. Preferably, Sp is a hydrocarbon group that may comprise oxygen, for example, in form of ether groups, but no other heteroatoms. In a particularly preferred embodiment, Sp is an alkylene group with 1 to 20, notably 1 to 10 and most preferably 1 to 6, notably 1 to 3 carbon atoms.

A specific example of a compound of formula (IV) is the compound below:

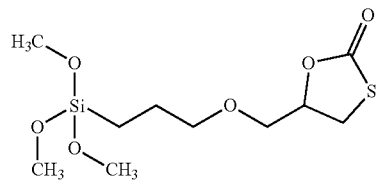

Preferred compounds B) with a silicon-functional group comprise one or two amino groups, particularly one amino group, and one alkoxysilane group $-SiR^{1s}R^{2s}R^{3s}$.

An example of compound B) with a silicon-functional group is trimethoxysilylpropyl amine.

Preferred compounds C) with a silicon-functional group comprise one or two functional groups, particularly one functional group, that react with a group —SH and one alkoxysilane group —SiR$^{1s}$R$^{2s}$R$^{3s}$.

Examples of compounds C) with a silicon-functional group are trimethoxysilylpropyl methacrylate and trimethoxysilylpropyl glycidylether.

To the process

According to the process of this invention, a compound A) with at least one five-membered cyclic monothiocarbonate group, and a compound B) with at least one amino group, selected from primary or secondary amino groups or blocked primary or secondary amino groups, hereinafter referred to as amino groups, and optionally a compound C) with at least one functional group that reacts with a group —SH are used as starting materials, whereby at least one of the compounds used as starting material comprises a silicon-functional group.

The principles of the reaction of compounds A), B) and optionally C) as well as details of the parameters of the reaction are described in WO 2019/034470 A1 and WO 2019/034473 A1.

The ring system of the five-membered cyclic monothiocarbonate group of compound A) is opened by the amino group of compound B), resulting in an adduct comprising a urethane group and a group —SH.

The group —SH of the adduct may be further reacted with a —SH reactive group, notably a non-aromatic ethylenically unsaturated group or an epoxy group of compound C) or also of compounds A) and B) as there exist also compounds A) or B) that comprise a non-aromatic, ethylenically unsaturated group, for example, 5-(methacryloyloxy)methyl-1,3-oxathiolane-2-one or 5-(acryloyloxy)methyl-1,3-oxathiolane-2-one (compounds C), allyl amine or aminoalkylvinylether (compounds B).

The group —SH reacts with the —SH reactive group. For example, the addition of a non-aromatic, ethylenically unsaturated group to —SH is known as Michael addition or thiol-ene reaction.

It should be mentioned that groups —SH that are not reacted may oxidize and will form disulfide bridges. Such oxidation may occur at room temperature in the presence of oxygen or other oxidants. Disulfide bridges may improve mechanical properties of the polymers obtained.

The obtained polymer comprises as structural element a urethane group with a sulfur atom being bonded via an ethylene group to the oxygen of the urethane group. This structural element can be represented by the following formula:

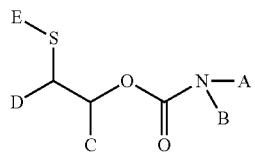

The variables A to E represent any possible substitutions by substituents.

The following statements apply to each of the three process alternatives b1) to b2) or, alternatively c1) to c2) or alternatively d1) to d3):

Compounds B) are preferably used in an amount to have 0.8 to 1.2 mol of amino groups of compound B) per 1 mol of five-membered cyclic monothiocarbonate groups of compound A) in the reaction mixture.

Preferably, the amount of functional groups that react with —SH is 0.5 to 1.2 mol per 1 mol of five-membered cyclic monothiocarbonate groups of compound A).

Preferably, the functional groups that react with —SH are groups of compound C).

Preferably, the starting materials are compounds A), B) and C).

Examples for combinations of compounds A), B) and C) that are reacted in the process steps are listed below, whereby the functional groups are abbreviated as follows:

Cyclic monothiocarbonate group of compound A): CTC

Primary amino group of compound B: PA

Functional group that reacts with —SH of compound C), A) or B): FG

Silicon-functional group: SIL a compound A) with two CTC, a compound B) with one PA and one SIL and a compound C) with one to five FG, preferably 2 to 5 FG;

a compound A) with two CTC, a compound B) with at least two PA and a compound C) with one FG (unsaturated group) and one SIL;

a compound A) with two CTC, a compound B) with at least two PA and a compound C) with one FG (epoxy group) and one SIL;

a compound A) with two CTC, a compound B) with one PA and a compound C) with one FG (epoxy group) and one SIL;

a compound A) with two CTC, a compound B) with one PA and a compound C) with one FG (unsaturated group) and one SIL.

Preferably, compounds A), B) and optionally C) are selected to give a mixture of A), B) and optionally C) that is liquid at 21° C., 1 bar. Such mixture does not require additional solvents to become liquid. For a liquid mixture of compounds A), B) and optionally C) it is sufficient that at least one, preferably two of the compounds A), B) and C) are liquid and thus are solvents for the remaining solid compound A), B) or C).

The reaction between compounds A), B) and optionally C) starts usually already at room temperature (about 20° C.) and may be completed at room temperature. The reaction may be supported by increasing the temperature of the coating composition or sealant, for example, up to 100° C. Alternatively or in addition, any activation energy for the reactions may be provided by high-energy radiation such as visible or UV-light. It is an advantage of the invention that the reaction easily occurs at low temperature and does not require supply of significant further energy such as high temperatures or high energy radiation.

Compounds A), B) or C) or any mixture thereof may comprise additives, such as stabilizers such as biocides, catalysts or additives that are desired or necessary for the intended final use of the cross-linked polymer, for example, colorants such as pigments. The catalysts include catalysts for the curing of the silicon-functional group, notably Sn comprising catalysts. Compounds A), B) or C) or any mixture thereof may comprise solvents. In a preferred embodiment no solvent is required, see above.

Preferably, the content of silicon in the polymer obtained by reacting compound A), B) and optionally C) is 0.001 to 0.4 mol Si per 100 g of the polymer, especially 0.001 to 0.3 mol Si per 100 g of the polymer.

More preferably, the content of silicon in the polymer obtained by reacting compound A), B) and optionally C) is 0.005 to 0.2 mol Si per 100 g of the polymer.

Most preferably, the content of silicon in the polymer obtained by reacting compound A), B) and optionally C) is 0.01 to 0.15 mol Si per 100 g of the polymer.

The above content of Si applies to the polymer obtained in step b1) as well as to the cross-linked polymer finally obtained by process steps b1) and b2), or, alternatively, by process steps c1) to c2) or by process steps d1) to d3).

Compounds A), B) and optionally C) are processed either by process steps b1) to b2), or, alternatively, by process steps c1) to c2) or by process steps d1) to d3).

The process of steps b1) to b2) is a two-step process. In process step b1) compounds A) and B) and optionally C) are reacted to form a polymer. Process step b1) is performed under exclusion of water. To avoid any humidity process step b1) may be performed under inert gas. The obtained polymer comprises silicon-functional groups that are still curable by water, notably humidity.

In process step b2) the polymer obtained is brought into the desired form, which is a coating, a filling or any other three-dimensional body. The silicon-functional groups cross-link with each other in the presence of any ambient water, for example, humidity or water supplied. Usually the normal humidity is sufficient to finally get a fully cross-linked polymer. The cross-linking process may be accelerated by providing further water. For example, water may be added to the polymer and the end of step b1) shortly before starting step b2).

In process steps c1) to c2) the compounds are first brought into the desired form, which is a coating, a filling or any other three-dimensional body, followed by a step c2) which is one step reaction including the formation of the polymer of A), B) and optionally C) as described above and simultaneously including the curing reaction of the silicon-functional groups. In process step c2) no humidity must be avoided. Process step c2) may be accelerated by providing further water.

In process step d1) to d3) curing of the silicon-functional groups occurs first, followed by the formation of the polymer of compounds A), B) and optionally C).

Therefore, the compound with the silicon-functional group, which may be a compound A), B) or C), is brought into the desired form and the silicon-functional groups are cured to give a silicon-based network. The compound with the silicon-functional group may be used in form of a mixture comprising any other compounds A), B) and C). However, it has to be avoided that the mixture comprises any combination of compounds A) and B). The mixture may comprise either compounds A) or, alternatively, compounds B) but not both, as the formation of the polymer of A), B) and optionally C) immediately starts with the ring-opening reaction of the amino group of B) with the monothiocarbonate group of A). In process steps d1) and d2) no humidity must be avoided. Process step d2) may be accelerated by providing further water.

The formation of the polymer of A), B) and C) follows in process step d3) by adding the missing compound B) or, alternatively, the missing compound A) to start the formation of the polymer. The missing compound A) or B) may be used in form of a mixture comprising compounds C).

Preferably, compounds A), B) and optionally C) are processed either by process steps b1) to b2), or, alternatively, by process steps c1) to c2).

More preferably, compounds A), B) and optionally C) are processed by process steps b1) to b2).

The coatings, fillings or other three-dimensional bodies obtained either by process steps b1) to b2), or, alternatively, by process steps c1) to c2) or by process steps d1) to d3) are fully cured and have good mechanical properties such as hardness and stiffness.

The process is useful to obtain coatings, a sealed material or a three-dimensional body for any technical application or any other purpose.

The process is useful for decorative, protective or functional coatings.

The process is useful for paints and lacquers which usually have the dual use to protect the substrate coated and to be decorative.

The process is useful for functional coatings which have the purpose to change or improve the surface properties of a substrate or to protect the surface of a substrate, for example, to improve adhesion, wettability, corrosion resistance or wear resistance. Functional coatings on fibers are often used as compatibilizers to improve interaction or adhesion between the polymer matrix and fibers in composites.

With the process of this invention silyl-modified polymers with urethane and sulfur functionality are obtained easily and economically. The process may be performed at room temperature without further supply of energy. The process does not require the use of isocyanates or starting materials with mercaptan groups. The process offers the possibility to prepare a variety of products, notably hybrid products having the benefits resulting from the content of sulfur, urethane and silyl cross-linking, which are, for example, mechanical properties in combination with chemical resistance, barrier properties, anti-static and anti-corrosion properties.

Compounds of formula (IV), for example, 5-(3-trimethoxysilylpropoxymethyl)-1,3-oxathiolane-2-one, provide a suitable alternative to known silanes such as trimethoxysilylalkyl-glycidylether which are well-known to form a siloxane network at ambient atmosphere.

Compounds of formula (IV) provide further the advantage, that a nucleohil reaction partner may selectively react with the cyclic monothiocarbonate unit allowing the release of the SH-functionality which offers a broad variety of follow-up reactions. Compound of formula (IV) may thus be employed as a chain extender rather than a reactive monomer.

Thus, compounds of formula (IV) represent a new building block for the synthesis of especially high molecular compounds and polymers. They may react as chain extender as well as allow a curing mechanism via siloxane linkages in orthogonal direction. Thus, an additional siloxane compound is not necessary. In case of employing amines as nucleophiles the reaction yields a valuable silane-functionalized urethane compound.

EXAMPLES

Following compounds have been used in the examples:
Compound A:
Bis-1,3-oxathiolane-2-one-5,5'-[1,4-butanediylbis(oxymethylene)] (BDO-CTC, prepared according unpublished application PCT/EP2019/081639), of formula:

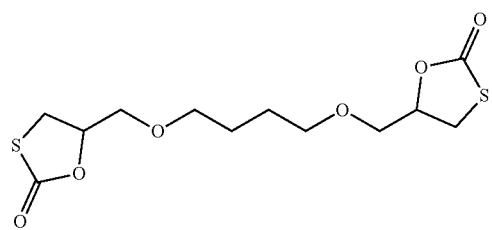 [SMILES: O=C1OC(COCCCCOCC2CSC(=O)O2)CS1]

5-(Methacryloyloxy)methyl-1,3-oxathiolane-2-one (MMA-CTC, prepared according to Example 8 of WO 2019/034469 A1) of formula

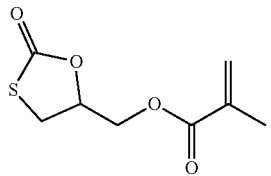

Compound B:
Butylamine
1,3-Bis(aminomethyl)cyclohexane (BAC) of formula

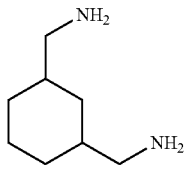

3-Aminopropyl-trimethoxysilane (APTMS)
Compound C:
Trimethoxysilylpropyl methacrylate (CAS 2530-85-0)
Trimethoxysilylpropyl glycidylether (3-(3-glycidyloxypropyl)trimethoxysilane (CAS 2530-83-8)
Trimethylolpropane trimethacrylate (TMPTMA, CAS 3290-92-4)
Bisphenol-A-glycerolate-dimethylacrylate (CAS 1565-94-2)
Diurethane-dimethacrylate (diurethane-DMA, CAS 72869-86-4)

Example 1: BDO-CTC+3-aminopropyl-trimethoxysilane+TMPTMA

Bis-1,3-oxathiolane-2-one-5,5'-[1,4-butanediylbis(oxymethylene)] (5 g) and TMPTMA (1.75 g) were mixed under stirring at room temperature. Subsequently, 3-aminopropyl-trimethoxysilane (5.5 g) was added, and stirring was continued for additional 3 min at room temperature, increasing viscosity over time. One part of the reaction mixture was transferred to a coating application via doctor blade (60 μm thickness) using various substrates (glass, steel). The other part of the reaction mixture was transferred to a cylindrical mold (diameter: 45 mm) and kept at ambient conditions. After 60 hours the second sample was cured yielding a hard and brittle specimen with uneven surface.

The coating proved to be completely dry after 1 hour at room temperature.

Example 2: BDO-CTC+BAC+trimethoxysilylpropyl methacrylate

Bis-1,3-oxathiolane-2-one-5,5'-[1,4-butanediylbis(oxymethylene)] (5 g) and 3-(trimethoxysilyl)-propyl methacrylate (7.7 g) were mixed under stirring at room temperature. Subsequently, 1,3-bis(aminomethyl)cyclohexane (2.2 g) was added, and stirring was continued for additional 3 min at room temperature showing an increase in temperature and viscosity. 5.5 g of the mixture were subsequently transferred to a cylindrical mold (diameter: 45 mm) and kept at ambient conditions. After 1 hour the sample showed skinning at the surface. The sample was completely cured overnight. The specimen showed significant shrinkage and hardness.

Example 3: BDO-CTC+BAC+trimethoxysilylpropyl glycidylether

Bis-1,3-oxathiolane-2-one-5,5'-[1,4-butanediylbis(oxymethylene)] (5 g) and trimethoxysilylpropyl glycidylether (7.3 g) were mixed under stirring at room temperature. Subsequently, 1,3-bis(aminomethyl)cyclohexane (2.2 g) was added, and stirring was continued for additional 3 min at room temperature showing an increase in temperature and viscosity. 5.5 g of the mixture were subsequently transferred to a cylindrical mold (diameter: 45 mm) and kept at ambient conditions. The sample showed skinning after 1 hour; after 5 hours the sample was nearly cured. The sample was completely cured over night. The transparent and flexible polymer showed flexibility and moderate brittleness

Example 4: BDO-CTC+butylamine+trimethoxysilylpropyl glycidylether

Bis-1,3-oxathiolane-2-one-5,5'-[1,4-butanediylbis(oxymethylene)] [5 g] and trimethoxysilylpropyl glycidylether (7.3 g) were mixed under stirring at room temperature. Subsequently, butylamine (2.26 g) was added, and stirring was continued for additional 3 min at room temperature showing an increase in temperature and viscosity. 5.5 g of the mixture were subsequently transferred to a cylindrical mold (diameter: 45 mm) and kept at ambient conditions. After 1 hour the sample showed skinning at the surface on top of the still viscous sample. The sample was completely cured within 58 hours at ambient conditions. The specimen was very brittle.

Example 5: BDO-CTC+butylamine+trimethoxysilylpropyl methacrylate

Bis-1,3-oxathiolane-2-one-5,5'-[1,4-butanediylbis(oxymethylene)] (5 g) and 3-(trimethoxy-silyl)propyl methacrylate (7.7 g) were mixed under stirring at room temperature. Subsequently, butylamine (2.26 g) was added, and stirring was continued for additional 3 min at room temperature showing an increase in temperature and viscosity. 5.5 g of the mixture were subsequently transferred to a cylindrical mold (diameter: 45 mm) and kept at ambient conditions. After 1 hour the sample showed skinning at the surface on top of still viscous sample. The sample was completely cured within 60 hours at ambient conditions. The specimen was very brittle.

Example 6: BDO-CTC+BPA-Gly-DMA+1,3-BAC+APTMS

Bis-1,3-oxathiolane-2-one-5,5'-[1,4-butanediylbis(oxymethylene)] (5 g) and bisphenol-A-glycerolate-dimethylacrylate (7.95 g) were mixed under stirring at room temperature. Subsequently, a mixture of 1,3-bis(aminomethyl)cyclohexane (1.1 g) and 3-aminopropyl-trimethoxysilane (2.78 g) was added under stirring. The mixture was homogenized, and stirring was continued at ambient conditions. The mixture increased in viscosity, and after 3 min the mixture was applied as a coating on steel via a doctor blade (60 μm thickness). The sample was kept at ambient temperature. After 60 min the coating showed surface skinning; the sample was completely cured within 24 hours at ambient conditions. The crosshatch test revealed excellent adhesion to the surface.

The content of silicon in the coated polymer was 0.1 mol Si/100 g polymer.

The silicon content (in mol) was calculated based on the used amounts of the starting materials, i.e., as silicon/total weight of the starting materials.

Example 7: BDO-CTC+MMA-CTC+Diurethane-DMA+APTMS+BAC

Bis-1,3-oxathiolane-2-one-5,5'-[1,4-butanediylbis(oxymethylene)] (5 g) and diurethane-dimethylacrylate (7.2 g) were mixed under stirring at room temperature followed by addition of 5-(methacryloyloxy)methyl-1,3-oxathiolane-2-one (2.0 g). Subsequently, a mixture of 1,3-bis(aminomethyl)cyclohexane (2.2 g) and 3-aminopropyl-trimethoxysilane (1.76 g) was added under stirring. The mixture was homogenized, and stirring was continued at ambient conditions. The mixture increased in viscosity, and after 3 min the mixture was applied as a coating on steel via a doctor blade (60 μm thickness). The sample was kept at ambient temperature. The coating was completely cured within 24 hours at ambient conditions.

The content of silicon in the coated polymer was 0.054 mol Si/100 g polymer.

Example 8: Synthesis of the Compounds of Formula (IV)

Compounds of formula (IV) may be prepared in accordance with the process described in WO 2019/034469 A1.

The compound of formula

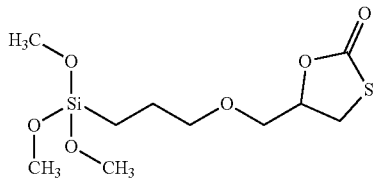 [SMILES: CO[Si](CCCOCC1CSC(=O)O1)(OC)OC]

was prepared in two steps as follows:

First step: Synthesis of [1-(chloromethyl)-2-(3-trimethoxysilylpropoxy)ethyl] carbonochloridate A 0.25 L stirred tank glass reactor equipped with two condensers (−30° C. and −78° C. (dry ice)) phosgene dip pipe and internal thermometer was purged with dry nitrogen overnight. Afterwards 113.6 g (0.47 mol, 1.00 eq.) of 3-glycidoxypropyltrimethoxysilane were introduced under nitrogen atmosphere. The cooling of the tank reactor was turned on and was adjusted to 15° C. After the reactor reached this temperature, 1.30 g (0.005 mol, 1.00 mol %) of tetrabutylammonium chloride (TBACl) were suspended in the starting material. Afterwards phosgene (overall 61 g, 0.67 mol, 1.31 eq.) was added to the reactor via the dip pipe. The temperature of the reaction mixture was continuously monitored and was kept below 20° C. by carefully adjusting the rate of the phosgene addition. Overall the addition took approximately 4 hours. After the phosgene addition was completed the initial cooling of the reactor was turned off, and the reactor was allowed to slowly reach room temperature. Afterwards the reaction mixture was stirred at room temperature for further 2 hours. Finally, the reaction mixture was stripped, with dry argon at room temperature, phosgene-free within 4 hours. The resulting colorless oil (151 g, 0.45 mol, 96% yield, regioisomeric purity: >95%) was directly used, without further purification, for the thiocarbonate formation.

Second step: Synthesis of 5-(3-trimethoxysilyl-propoxymethyl)-1,3-oxathiolane-2-one

[1-(chloromethyl)-2-(3-trimethoxysilylpropoxy)ethyl] carbonochloridate (20 g, 0.06 mol) and acetonitrile (50 mL) were placed in a 250 mL 4 neck round bottom flask equipped with a KPG crescent stirrer, dropping funnel, thermometer and a reflux condenser. The solution was cooled down to 0° C. with an ice bath before solid $Na_2S$ (1 eq.) was slowly added, maintaining the temperature at 5° C. After the complete addition the ice bath was removed, and the reaction mixture was allowed to warm to room temperature. After stirring for 4 hours the suspension was filtered, and the solvent was removed under reduced pressure. The crude cyclic thiocarbonate was obtained as a clear oil (17 g, 95%).

The invention claimed is:

1. A process for the preparation of a substrate applied with a cross-linked polymer, comprising urethane groups and silicon atoms, the process comprising:
   a) providing a compound A), a compound B), and optionally a compound C), for a reaction according to b1) to b2), c1) to c2), or d1) to d3),
   wherein the compound A) comprises at least one five-membered cyclic monothiocarbonate group,
   wherein the compound B) comprises at least one amino group, selected from the group consisting of primary amino groups, secondary amino groups, blocked primary amino groups, and blocked secondary amino groups,
   wherein the compound C), if present, comprises at least one functional group that reacts with a group —SH, and
   whereby at least one of compounds A), B), and optionally C) comprises a silicon-functional group;
   b1) reacting compounds A) and B), and optionally C), under exclusion of water to obtain a polymer with silicon-functional groups that are still curable, and
   b2) applying the polymer obtained in b1) to a surface, gap, or a three-dimensional template, and curing the silicon-functional groups with ambient water;
   or, alternatively,
   c1) applying compounds A) and B), and optionally C), to a surface, gap, or a three-dimensional template, and
   c2) reacting compounds A) and B), and optionally C), and curing the silicon-functional groups with ambient water in one step;
   or, alternatively,
   d1) applying the compound A) with a silicon-functional group, the compound B) with a silicon-functional group, the compound C) with a silicon-functional group, or a mixture comprising compounds A) and C) or B) and C), whereby such mixture does not comprise compounds A) and B) in combination, to a surface, gap, or a three-dimensional template, and
   d2) curing the silicon-functional groups with ambient water, and
   d3) adding compounds A), B), and optionally C), which have been provided but not yet applied and reacting these compounds.

2. The process according to claim 1, wherein the compound A) is
a compound of formula (I)

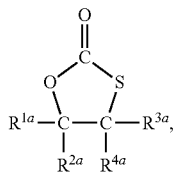

with $R^{1a}$ to $R^{4a}$ independently from each other representing hydrogen or an organic group with up to 50 carbon atoms,
whereby, alternatively, $R^{2a}$, $R^{4a}$, and the two carbon atoms of the thiocarbonate group together form a five to ten membered carbon ring; or
a compound of formula (II)

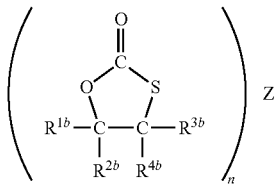

with $R^{1b}$ to $R^{4b}$ independently from each other representing hydrogen or an organic group with up to 50 carbon atoms,
whereby, alternatively, $R^{2b}$, $R^{4b}$, and the two carbon atoms of the monothiocarbonate group together form a five to ten membered carbon ring, and
with one of the groups $R^{1b}$ to $R^{4b}$ being a linking group to Z,
n representing an integral number of at least 2, and
Z representing a n-valent organic group.

3. The process according to claim 1, wherein the compound B) comprises one to five amino groups.

4. The process according to claim 1, wherein the at least one functional group of compound C) that reacts with —SH is selected from the group consisting of a non-aromatic, ethylenically unsaturated group and an epoxy group.

5. The process according to claim 1, wherein the compound B) comprises the silicon-functional group.

6. The process according to claim 1, wherein the silicon-functional group is an alkoxysilane group of formula —$SiR^{1s}R^{2s}R^{3s}$,
wherein at least one of the groups $R^{1s}$ to $R^{3s}$ is an alkoxy group and the other groups $R^{1s}$ to $R^{3s}$ are hydrogen or an alkyl group.

7. The process according to claim 6, wherein two or three of the groups $R^{1s}$ to $R^{3s}$ are an alkoxy group and a remaining group $R^{1s}$ to $R^{3s}$, if present, is an alkyl group.

8. The process according to claim 1, wherein a mixture of compounds A), B), and optionally C) is liquid at 21° C. and 1 bar.

9. The process according to claim 1, wherein b1) to b2) are performed.

10. The process according to claim 1, wherein a content of silicon in the cross-linked polymer comprising urethane groups and silicon atoms is 0.001 to 0.3 mol silicon per 100 g of the polymer.

11. A coating, a sealed material, or a molded body, obtainable by the process as defined in claim 1.

12. A polymer, obtained by reacting a compound A), a compound B), and optionally a compound C),
wherein the compound A) comprises at least one five-membered cyclic monothiocarbonate group,
wherein the compound B) comprises at least one amino group, selected from the group consisting of primary amino groups, secondary amino groups, blocked primary amino groups, and blocked secondary amino groups,
and wherein the compound C), if present, comprises at least one functional group that reacts with a group —SH;
wherein at least one of compounds A), B), and optionally C), comprises a silicon-functional group, and
wherein the polymer comprises 0.001 to 0.3 mol of silicon per 100 g of the polymer.

13. A compound, comprising one or two five-membered cyclic monothiocarbonate groups and one alkoxysilane group —$SiR^{1s}R^{2s}R^{3s}$,
wherein at least one of the groups $R^{1s}$ to $R^{3s}$ is an alkoxy group and the other groups $R^{1s}$ to $R^{3s}$ are hydrogen or an alkyl group.

14. The compound according to claim 13, wherein the compound is a compound of formula (IV)

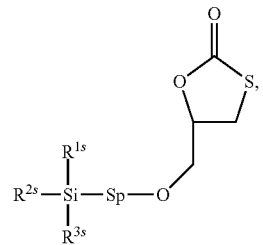

wherein at least one of the groups $R^{1s}$ to $R^{3s}$ is an alkoxy group, and the other groups $R^{1s}$ to $R^{3s}$ are hydrogen or an alkyl group, and
wherein Sp is a spacer group, which is an organic group with 1 to 20 carbon atoms.

* * * * *